United States Patent [19]  [11] 4,164,937
Spencer  [45] Aug. 21, 1979

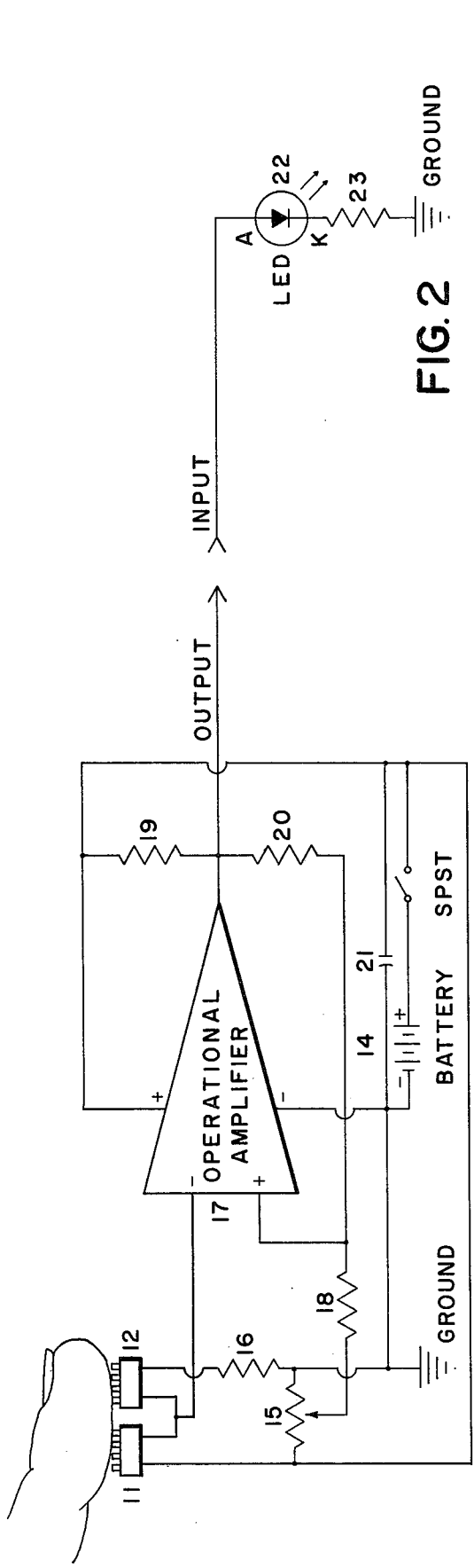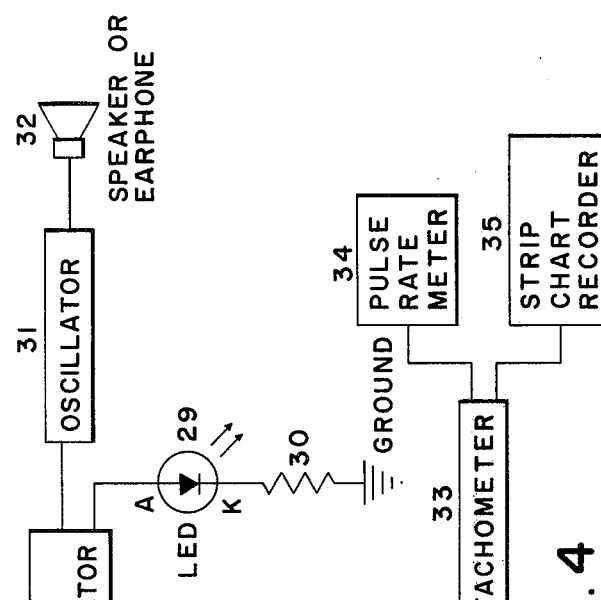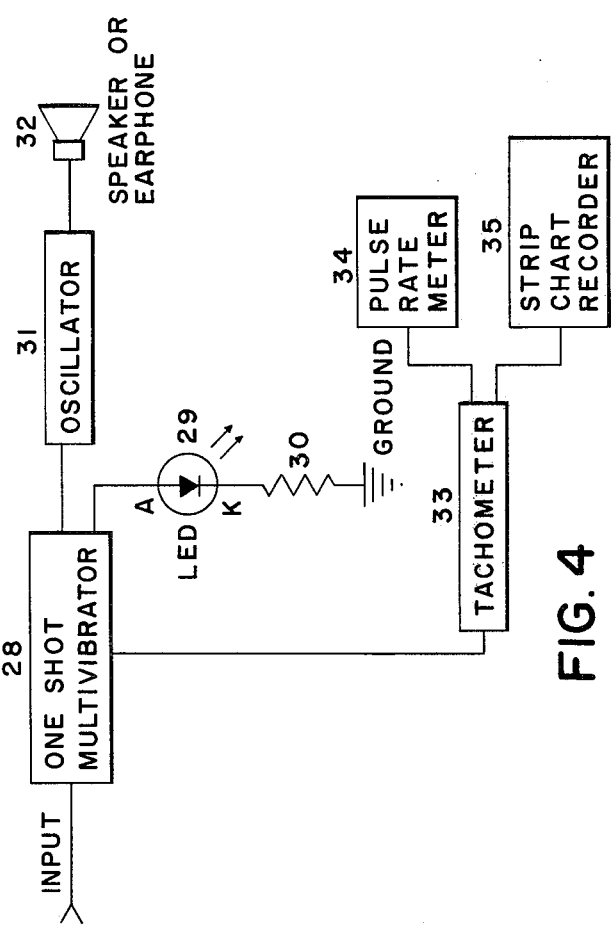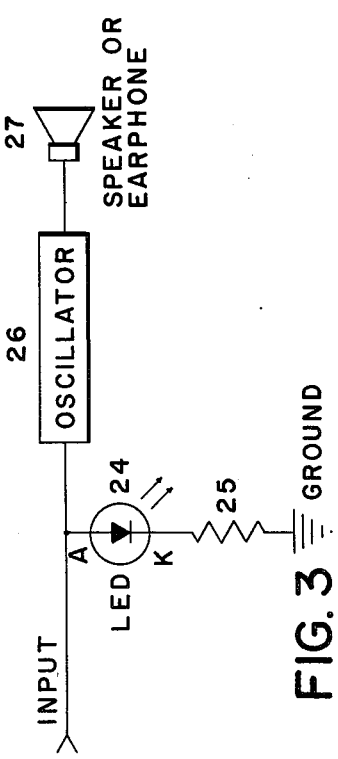

[54] EQUIPMENT FOR DETECTING, MONITORING, MEASURING, DISPLAYING AND RECORDING PULSE AND HEARTBEAT

[76] Inventor: William E. Spencer, 3201 MacVicar Ct., Topeka, Kans. 66611

[21] Appl. No.: 748,153

[22] Filed: Dec. 2, 1976

[51] Int. Cl.² ............................................. A61B 5/02
[52] U.S. Cl. .................................... 128/666; 128/688; 128/689
[58] Field of Search ...................... 128/2.05 P, 2.05 T, 128/2.05 R, 2.05 E, 2.06 R, 2.06 F

[56] References Cited

U.S. PATENT DOCUMENTS

| | | | |
|---|---|---|---|
| 2,848,992 | 8/1958 | Pigeon | 128/2.05 P |
| 3,176,681 | 4/1965 | Smith | 128/2.05 P |
| 3,742,938 | 7/1973 | Stern | 128/2.05 T |
| 3,830,227 | 8/1974 | Green | 128/2.06 R |
| 3,835,837 | 9/1974 | Peek | 128/2.05 P |
| 3,903,873 | 9/1975 | Royal et al. | 128/2.05 P |
| 3,993,047 | 11/1976 | Peek | 128/2.05 P |
| 4,030,484 | 6/1977 | Kuska et al. | 128/2.05 P X |
| 4,052,979 | 10/1977 | Scherr et al. | 128/2.05 P |

FOREIGN PATENT DOCUMENTS 238075 10/1969 U.S.S.R. ............................... 128/2.05 P

Primary Examiner—Lee S. Cohen

[57] ABSTRACT

An inexpensive, compact and portable instrument using two photoelectric cells in a sensitive Wheatstone bridge, an operational amplifier and ambient light sources and arranged to easily engage the finger or other parts of the human body at frequent intervals and detect the pulsatile blood changes in the vascular bed and provide a visual and audible indication corresponding to the pulse and heartbeat. Also, the pulse and heartbeat can be measured and the pulse ratetime patterns recorded for various diagnostic purposes including the identification of suspected allergens and toxic substances.

3 Claims, 4 Drawing Figures

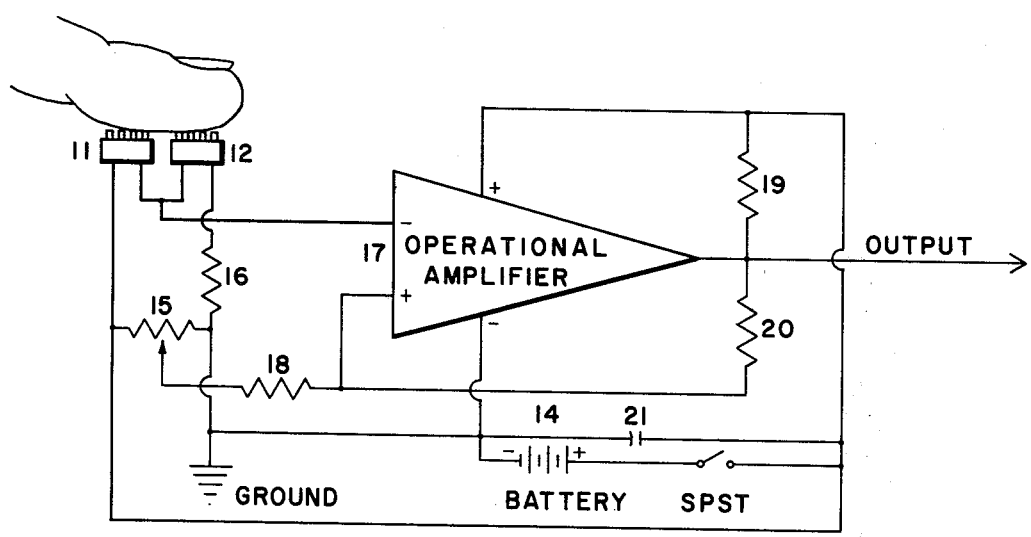

EQUIPMENT FOR DETECTING, MONITORING, MEASURING, DISPLAYING AND RECORDING PULSE AND HEARTBEAT

BACKGROUND OF THE INVENTION

This invention is in the field of pulse and heartbeat detecting, monitoring, measuring, displaying and recording systems.

Suspected ingested and inhaled allergens and toxic substances have been detected and identified in human subjects by noting changes in the pulse rate or heart rate at specific time intervals. "THE PULSE TEST" by Dr. A. C. Coca, M.D., Arc Books, Inc., N.Y. describes in detail a method of detecting and identifying suspected allergens within several hours after ingestion. The inventor of this invention has discovered and developed an experimental method of detecting and identifying suspected allergens and toxic substances within several minutes after ingestion or inhalation of an allergen or toxic substance. Both methods are based on changes in the pulse rate and depend on frequent and accurate measurements of the subject's pulse.

The pulse and heartbeat rate is a basic parameter used to help evaluate the condition of the human body. The most common method of determining an individual's pulse rate is to locate the pulse, observe a sweep second hand on a timepiece and mentally count for a specific time period. The number of pulses counted over a fraction of a minute is multiplied by a factor to obtain the pulse rate which is normally stated in pulses or heartbeats per minute. This method is time consuming and inaccurate due to difficulties in finding and identifying the pulse, human errors in counting and computing the pulse rate and inherent errors in multiplying pulse counted in short periods by a factor. Also, beatbybeat variations in pulse rate can significantly effect the results particularily if the pulses are counted over a short period. This procedure is not wellsuited for detecting and identifying allergens and toxic substances where frequent or continuous measurements are needed.

Prior art discloses photocell transducers for detecting peripheral pulsations using a light source in combination with a single photocell. In some applications, the vascular bed is placed between the light source and photodetector and the capillary pulse changes the transmitted light. In other applications, the light source is placed adjacent to the photodetector and the pulse changes the amount of reflected and scattered light.

The problem of detecting, monitoring, measuring and displaying the pulse and heartbeat has long resisted the development of a simple, economical, compact and portable instrument that could be used at frequent intervals by large segments of the population.

SUMMARY OF THE INVENTION

An inexpensive battery operated, self-contained, light-weight, compact, portable integrated circuit instrument that detects the pulsatile blood volume changes in the finger or other parts of the human body and provides a visual indication and audible tone corresponding to the pulse and heartbeat of the subject. Also, the pulse and heartbeat repetition rate can be measured on an analog or digital meter in pulse or heartbeats per minute. In addition, the pulse rate-time patterns can be recorded using commercially available strip chart recording devices.

Experiments have indicated that suspected ingested and inhaled allergens and toxic substances can be identified by observing changes in pulse and heart rate with respect to time and/or analysing pulse ratetime patterns using this invention. Also, experiments indicate the relative toxicity of a suspected allergen or toxic substance can be determined, a suspected allergen or toxic substance can be identified in an unknown substance by comparing with the pulse rate-time pattern of a known allergen or toxic substance and the threshold level and safe exposure level of an allergen or toxic substance can be approximated.

Two photoconductive cells are used to form arms of a very sensitive Wheatstone bridge and placed in a differential configuration to reduce the effect of changing and unregulated ambient light sources reaching the cells. The intensity of ambient light from interior and/or exterior light sources striking both photoconductive cells is changed or modulated by blood volume changes in the finger or other parts of the human body placed on the photocells. The subject can balance the bridge using several methods such as adjusting the position of his finger on the two photocells. The instrument is designed to be easily used at frequent intervals by large segments of the population.

OBJECTIVES OF THE INVENTION

One objective of this invention is to provide a new and improved pulse and heart rate detecting, monitoring, measuring and display instrument using integrated circuits which is simple, inexpensive, battery-operated, self-contained, light-weight, compact and portable.

A further objective of this invention is to provide a pulse and heartbeat monitor that activitates a light source and gives an audible signal with each heartbeat to give an immediate indication of the heart rhythm and abnormalities or irregularities in the pulse and heartbeat such as skipping or adding beats.

A further objective of this invention is to provide an instrument which may be easily and frequently used by a subject to monitor and accurately measure his pulse and heartbeat on a continuous basis or at intermittent intervals and obtain a permanent record of pulse rate over a period of time.

A further objective of this invention is to provide a pulse and heart rate detecting, monitoring, measuring, display and recording instrument to assist in the identification of allergens and toxic substances.

These and other objectives of this invention will become apparent to those skilled in the art from the following detailed description of the preferred embodiment and associated drawings.

BRIEF DESCRIPTION OF THE DRAWINGS

FIG. 1 is a schematic diagram of a photoconductive cell transducer including an operational amplifier circuit. This equipment is used to detect the pulse and heartbeat.

FIG. 2 is a schematic diagram of a simple visual display. Equipment in FIG. 1 and FIG. 2 is used to detect, monitor and display the pulse and heartbeat.

FIG. 3 is a schematic diagram of a simple visual display and block diagram of an audible tone source. Equipment in FIGS. 1 and 3 is used to detect, monitor and display the pulse and heartbeat.

FIG. 4 is a schematic diagram of a simple visual display and block diagram of an audible tone source, tachometer, pulse rate meter and strip-chart recorder.

Equipment in FIGS. 1 and 4 is used to detect, monitor, measure, display and record the pulse and heartbeat.

DESCRIPTION OF THE PREFERRED EMBODIMENTS

Referring to FIG. 1, commerically available plastic cases can be used to house the integrated circuits and other components. Two identical photoconductive cells 11 and 12 are mounted together on the top surface of the case so that the subject's finger or other parts of the human body can be placed over both cells at the same time.

Photoconductive or photoresistive cells are very sensitive light detectors with dark to light ratios of up to 10,000:1 and more. The conductance is nearly linear with light intensity and resistance varies reciprocally with intensity. The most common cells for detection of visible light consists of an insulating substrate with thin layers of cadmium sulfide (CdS) or cadmium selenide (CdSe). Electrical connections are made to the material and the entire cell is housed in a protective enclosure with a transparent window or coated with a protective layer of clear plastic. A photoconductive cell with reasonably fast response time at low light levels is needed in this application. Also, the sensitivity of the cells should not be affected by light levels of sufficient intensity to temporarily change its response to subsequent lower light levels since this could temporarily impair the stability of the transducer. In addition, the cell should have good sensitivity in the visible light spectra in order for this instrument to be effective with all ambient light sources. Photoconductive cells such as the cadmium sulphide photocell No. 276-129 from Radio Shack have the necessary physical and electrical characteristics.

In most photocell applications, a constant-intensity light source with a regulated lamp voltage is required. Also, shielding to prevent stray light from other sources is generally required. This invention does not require a separate light source with associated regulated power or shielding from stray light. Instead, natural or artifical ambient light is used.

Photocell 11, photocell 12, potentiometer 15 and fixed resistor 16 are arranged in a very sensitive resistor type Wheatstone bridge. The D.C. power supply 14 provides power for the Wheatstone bridge and operational amplifier integrated circuit 17. Fixed resistor 16 is used to reduce the power consumption and desensitize the photocell 12 when the subject uses his finger 13 in a sliding motion to balance the bridge. Potentiometer 15 can also be used to balance the bridge. In addition, the relative position of the instrument and ambient light source and various methods of limiting ambient light can be used to balance the bridge.

The sensitivity of the Wheatstone bridge near the point of balance depends upon the value of the battery supply voltage 14, value of the resistances in the arms and sensitivity of the operational amplifier 17. The Wheatstone bridge is balanced with zero or near zero voltage at the input of the operational amplifier 17. For each pulse and heartbeat, fresh blood is pumped into the capillaries. The intensity of ambient light transmitted through the vascular bed is proportional to the amount of blood flowing and redness (oxygen saturation), thereby causing a periodic increase and decrease in light intensity detected by the photocells. When the bridge is properly adjusted, pulsatile blood volume changes in the finger placed on the two photocells changes the bridge from a balanced to unbalanced state for each pulse and heartbeat.

The operational amplifier integrated circuit 17 senses the balanced and unbalanced state of the Wheatstone bridge. The No. 339 quad comparator and other operational amplifier integrated circuits have the necessary electrical characteristics for this function. The No. 339 comparator is an operational amplifier with low current drain using a single supply voltage especially designed to operate in the open-loop mode without a feedback resistor. The No. 339 comparator senses the bridge output and converts differences in low-level analog signals to a high level digital output. Resistor 18 is used to set the input threshold trip voltage and may be omitted in some applications. The fixed resistor 19 or output pull-up resistor should be high enough to avoid excessive power dissipation yet low enough to supply sufficient drive to switch the load on the comparator circuit. Resistor 20 adds a small amount of positive feedback or hysteresis to prevent oscillations when the comparator input signal is a slowly varying low level signal. Stray coupling between the output and input leads can cause unwanted oscillations and erratic operation. Consquently, these leads should be short and separated. The fixed capacitor 21 across the power supply 14 prevents certain unwanted oscillations caused by long power leads. A small 9 volt battery can be used for the power supply 14 and will not create an electrical hazard.

The output voltage of the operational amplifier 17 using the No. 339 comparator swings from one extreme to the other without any intermeadiate levels and can be used to operate a light emitting diode (LED) 22 with suitable current limiting resistor 23 as shown in FIG. 2. The output voltage of FIG. 1 can also be used to drive a light emitting diode (LED) 24 with a suitable current limiting resistor 25 and oscillator circuit 26 and associated speaker or earphone 27 in FIG. 3. The No. 339 comparator and other commerically available integrated circuits can be arranged with suitable additional components to generate audible tones in the 600 to 1000 herz frequency range.

Referring to FIG. 4, a one-shot multivibrator 28 can be driven by the output of the comparator circuit 17 in FIG. 1. A standard 7400 multivibrator or 339 comparator integrated circuit can be used with suitable timing resistors and capacitors to provide a measured output pulse with input trigger lock-out to insure the circuit will not re-trigger before completion of the output pulse.

The output of the one-shot multivibrator 28 can be used to drive a light emitting diode (LED) 29 with suitable current limiting resistor 30 and oscillator circuit 31 and associated speaker or earphone 32 in FIG. 4. Also, the output of the one-shot multivibrator can be used to drive a tachometer circuit 33 consisting of a current limiting resistor and an integrating capacitor in parallel with an analog or digital meter 34 calibrated in pulse or heartbeats per minute and in series with a current limiting resistor connected to ground. In place of the integrating capacitor, the LM 3900 integrated circuit with suitable components as covered in LINEAR APPLICATIONS, Volume 1, Radio Shack Catalog No. 621373, page AN 72-33, FIGS. 78 and 79 can be used. The DC output signal produced by the tachometer circuit 33 using either an integrated circuit or integrated capacitor is proportional to the pulse and heartbeat rate.

Also, the tachometer circuit 33 can be arranged to drive a strip chart recorder 35 calibrated in pulse or heartbeats per minute to produce a permanent record of the pulse and heartbeat rate over a period of time. However, the strip chart recorder limits the portability of this invention since these recorders generally operate from alternating current supplies.

In addition, a current or voltage sensing circuit such as the Schmitt trigger circuit with adjustable input threshold levels can be arranged to monitor the output of the tachometer 33 in FIG. 4. When the input signal to the Schmitt trigger is increased or decreased to a predetermined point representing a maximum or minimum limit of pulse and heartbeat rate, an output signal from the Schmitt trigger circuit would operate a visual and/or audible alarm signal.

Also, an analog pulse rate meter 34 can be equipped with a reference needle to identify by visual and audible alarm the predetermined maximum and minimum limits of pulse and heartbeat rates.

An astable multivibrator with variable frequency and duty cycle connected to the input of the operational amplifier 17 or subject with uniform pulse can be used with an accurate timepiece to check and calibrate the pulse rate meter and strip chart recorder shown in FIG. 4. The multivibrator could also be used to establish predetermined maximum and minimum limits of pulse and heartbeat rates that would operate the visual and audible alarms.

The mode of operation of the invention depends on availability and use of the visual and audible indicators covered in FIGS. 2, 3 and 4. The bridge can be balanced using either visual or audible indications. Also, the bridge can be balanced using both visual and audible indications.

The subject can stand, sit or recline in an area with adequate natural or artificial ambient light of reasonably uniform intensity and simply place his finger or other parts of the human body on the two photocells. Best results are obtained by operating this instrument within several feet of a table lamp with a tungsten filament. If the bridge is unbalanced, there will be either no visual and audible indications or continuous visual and audible indications. The subject simply balances the bridge by adjusting the bridge from an absence of visual and audible indications toward continuous visual and audible indications or by adjusting the bridge from continuous visual and audible indications toward an an absence of visual and audible indications. This adjustment is made by (1) varying the position of the finger 13 on the two cells 11 and 12 in a sliding motion in the position shown in FIG. 1, (2) varying the position of the instrument with the light source (or sources), (3) varying the intensity of the light source (or sources) and/or (4) adjusting the potentiometer 15 to compensate for variations in light intensity, light sources and size, shape, color, etc of the subject's finger.

A balanced or near balanced bridge will produce visual and audible indications in response to blood flow changes and corresponding to the pulse and heartbeat. The pulse and heartbeat rate can be determined by mentally counting for a specific time period and multiplying this by a factor to obtain the pulse and heartbeat rate per minute. With FIG. 4 and FIG. 1, the pulse rate meter will give the pulse and heartbeat rate and the strip chart recorder will provide a permanent record.

Using this invention, experiments have indicated that suspected ingested and inhaled allergens and toxic substances can be identified by observing changes in pulse and heart rate with respect to time and/or analyzing pulse rate-time patterns. Also, experiments indicate the relative toxicity of a suspected allergen or toxic substance can be determined, a suspected allergen or toxic substance can be identified in an unknown substance by comparing with the pulse rate-time pattern of a known allergen or toxic substance and the threshold level and safe exposure level of an allergen or toxic substance can be approximated. Although most measurements are best made in the sitting or reclining position, this instrument can be moved to identify the source of an inhaled allergen or toxic substance.

This portable, self-contained instrument is designed to be easily used at frequent intervals. As an alternative, the two photoconductive cells can be incorporated into a pad which can be placed, held or attached to a suitable part of the body. Also, monitoring, measuring and displaying of the pulse and heartbeat can be performed at a central location using one or more transducers at remote locations.

The foregoing description taken together with the appended claims constitute a disclosure such as to enable a person skilled in optoelectronics and biomedical instrumentations and having the benefit of teachings contained herein to make and use the invention and generally constitutes a meritorious advance in the art unobvious to such a skilled worker not having the benefit of these teachings.

Obviously many modifications and variations to those referred to above can be made without departing from the scope of the invention as defined by the appended claims. In particular and as mentioned above, the transducer can be incorporated into a pad which can be placed on some suitable part of the body. Only the preferred embodiments have been shown and described and that all changes and modifications that come within the spirit of the invention and the scope of the claims are also desired to be protected.

What is claimed and desired to be secured by Letters Patent of the United States is:

1. Apparatus for detecting, monitoring and displaying the pulse and heartbeat of a human subject consisting of:
   a. a transducer for engaging the finger and other parts of the human body to form optically created pulse signals from pulsatile blood volume changes using ambient light sources wherein said transducer consists of two photocells and a potentiometer, means for positioning the photocells to allow the photocells to detect ambient light transmitted through an engaged finger or other body parts and the photocells and potentiometer being connected as arms of a Wheatstone bridge circuit with said photocells being connected in a differential configuration to reduce the effect of changing and unregulated light sources and provide a suitable low level analog signal from minute photocell resistance changes and permit simple adjustments of the Wheatstone bridge circuit by varying the position of subject's finger on the transducer, varying the effect of ambient light sources on the transducer and/or varying the potentiometer in the Wheatstone bridge circuit;
   b. comparator circuit means connected to the Wheatstone bridge circuit that senses the state of the Wheatstone bridge circuit and converts said low level analog signal to a high level digital output signal in response to the optically created pulse signals; and c. a light indicator connected to the comparator circuit means and operated by said comparator circuit means to produce a visual signal corresponding to the pulse and heartbeat.

2. Apparatus for detecting, monitoring and displaying the pulse and heartbeat according to claim 1 wherein a signal generator and associated speaker are connected to and operated by the comparator circuit means to produce an audible signal corresponding to the pulse and heartbeat.

3. Apparatus for detecting, monitoring and displaying the pulse and heartbeat according to claim 1 wherein a multivibrator is connected to and operated by the comparator circuit means to produce a timed output pulse, the apparatus further comprising of:

a. a signal generator and associated speaker connected to the multivibrator to produce an audible signal corresponding to the pulse and heartbeat;

b. said light indicator being connected to the comparator circuit means through multivibrator to produce a visual indication corresponding to the pulse and heartbeat; and c. a tachometer connected to the multivibrator to produce a linear analog output proportional to the pulse or heartbeat rate and further comprising of:
  1. an analog or digital meter with a scale graduated in pulse or heartbeats per minute connected to the tachometer to provide a visual indication corresponding to the pulse rate and heartbeat rate; and
  2. a strip chart recorder with a scale graduated in pulse or heartbeats per minute connected to the tachometer to provide a permanent record corresponding to the pulse rate and heartbeat rate over a period of time.

* * * * *